United States Patent
Meese

(10) Patent No.: US 6,858,650 B1
(45) Date of Patent: Feb. 22, 2005

(54) STABLE SALTS OF NOVEL DERIVATIVES OF 3,3-DIPHENYLPROPYLAMINES

(75) Inventor: Claus Meese, Monheim (DE)

(73) Assignee: Schwarz Pharma AG (DE)

( * ) Notice: Subject to any disclaimer, the term of this patent is extended or adjusted under 35 U.S.C. 154(b) by 0 days.

(21) Appl. No.: 10/130,214

(22) PCT Filed: Nov. 15, 2000

(86) PCT No.: PCT/EP00/11309

§ 371 (c)(1), (2), (4) Date: May 14, 2002

(87) PCT Pub. No.: WO01/35957

PCT Pub. Date: May 25, 2001

(30) Foreign Application Priority Data

Nov. 16, 1999 (DE) .......................... 199 55 190

(51) Int. Cl.[7] .................. A01N 37/08; A01N 37/12; A01N 37/44; A61K 31/215; A61N 31/24

(52) U.S. Cl. .................. 514/530; 514/531; 514/534; 514/548; 514/551; 560/61; 560/122; 560/123; 560/124; 560/138; 560/142; 560/250; 564/319

(58) Field of Search ................ 514/530, 531, 514/534, 548, 551; 560/61, 122, 123, 124, 138, 142, 250, 37, 18, 42, 140; 564/319

(56) References Cited

U.S. PATENT DOCUMENTS 5,686,464 A 11/1997 Johansson et al. .......... 514/315

FOREIGN PATENT DOCUMENTS

| DE | 693 17 898 T2 | 10/1998 | ......... C07C/217/62 |
|----|---|---|---|
| EP | 0 667 852 B1 | 4/1998 | ......... C07C/217/62 |
| EP | 0 957 073 A1 | 11/1999 | ............ C07C/1/00 |
| WO | 9411337 | 5/1994 | |
| WO | 9843942 | 10/1998 | |
| WO | 9958478 | 11/1999 | |

OTHER PUBLICATIONS

Nilvebrant et al, "Antimuscarinic Potency and Bladder Selectivity of PNU–200577, a Major Metabolite of Tolterodine" Pharmacology and Toxicology. vol. 81, pp. 169–172 (1997).*

L. Palmer, L. Andersson, T. Andersson, U. Stenberg: *Determination of tolterodine and the 5–hydroxymethly metabolite in plasma, serum and urine using gas chromatography–mass spectrometry; Journal of Pharmaceutical and Biomedical Analysis*; Jan. 20, 1997; pp. 155–165.

* cited by examiner

Primary Examiner—Richard L. Raymond
Assistant Examiner—Zachary C. Tucker
(74) Attorney, Agent, or Firm—Peter F. Corless; Christine C. O'Day; Edwards & Angell, LLP

(57) ABSTRACT

The present invention concerns highly pure, crystalline, stable compounds of novel derivatives of 3,3-diphenylpropylamines in the form of their salts, a method for the manufacture and highly pure, stable intermediate products.

The method is in particular characterized by regio- and chemoselectivity and high yield. Salts of phenolic monoesters of 3,3-diphenylpropylamines are provided, that are particularly well-suited for use in pharmaceutical formulations. Preferred compounds are R-(+)-2-(3-diisopropylamino-1-phenyl-propyl)-4-hydroxymethylphenylisobutyrate ester hydrogen fumarate and R-(+)-2-(3-diisopropylamino-1-phenylpropyl)-4-hydroxymethylphenylisobutyrate ester hydrochloride hydrate. Furthermore, stable, crystalline intermediate products that are essential for obtaining the abovementioned salts are provided. A preferred intermediate product is R-(−)-3-(3-diisopropylamino-phenyl-propyl)-4-hydroxy-benzoic acid methyl ester.

24 Claims, 1 Drawing Sheet

Reaction diagram 1

(i), (ii), (iii), (iv), (v) stand for: (i), LiAlH$_4$, (ii), Raney nickel/H$_2$, (iii), Me$_2$CH-COCl, Et$_3$N, (iv), fumaric acid, (v), hydrochloric acids; R stands for isopropyl (iPr)

STABLE SALTS OF NOVEL DERIVATIVES OF 3,3-DIPHENYLPROPYLAMINES

This application was filed under 35 U.S.C. 371, and is the U.S. National Stage of PCT/EP00/11309, filed 5 Nov. 2000.

This patent application claims the benefit of priority under 35 U.S.C. §119 of German Patent Application No. 199 55 190.1, filed Nov. 16, 1999. German Patent Application No. 199 55 190.1 is incorporated herein in its entirety by reference.

The present invention concerns highly pure, crystalline, stable compounds of novel derivatives of 3,3-diphenylpropylamines in the form of their salts, a method for manufacturing these and highly pure, stable, intermediate products.

From document PCT/EP99/03212 novel derivatives of 3,3-diphenylpropryrlamines are known.

These are valuable prodrugn for the treatment of urinary incontinence and other spasmodic complaints, which overcome the disadvantage of the active substances available to date, namely inadequate absorption of the active substance by biological membranes or the unfavourale metabolism of these.

Furthermore these novel prodrugs have improved pharmacokinetic characteristics compared with Oxybutynin and Tolterodin.

Preferred compounds from the group of these novel derivatives of 3,3-diphenylpropylarines are esters of aliphatic or aromatic carboxylic acids with the general formula A referred to below

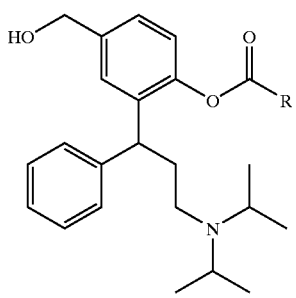

Formula A in which R denotes $C_1$–$C_6$-alkyl, $C_3$–$C_{10}$-cycloalkyl or unsubstituted or substituted phenyl. These can occur in their optical isomers form as racemic mixtures and in the form of their individual enantiomers.

Compounds with the structure of formula A do, however, have low solubility in water. This restricts their oral bio-availability.

Finally, monoesters of the structure, as shown in formula A, have a tendency towards intermolecular transesterification. During long periods of storage, therefore, as the content of the compounds with the structure of general formula A drops an increase in diesters and free diol can be detected.

Basically salts of the compounds of general formula A can be obtained if solutions of the compounds of formula A (base component) are purified with solutions of acids in suitable solvents, but the salts obtained in the form of solid matter can prove to be altogether amorphous and/or hygroscopic and cannot be directly crystallized from the normal solvents either. Such salts have inadequate chemical stability to be galenically processed as valuable pharmaceutically active substances.

Surprisingly, it has now been found that the abovementioned disadvantages can be avoided if compounds with the structure of general formula A, once they have been prepared under a special reaction process, are converted with a physiologically compatible inorganic or organic acid with general formula H-X, in which $^-$X represents the respective acid residue, into their respective salt with general formula I.

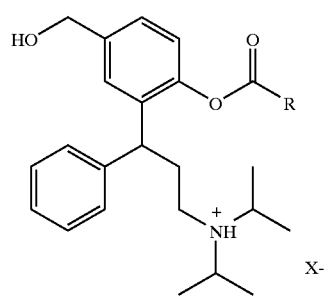

Formula I

The problem for the present invention is therefore to provide highly pure, crystalline, stable compounds of novel derivatives of 3,3-diphenylpropylamines in the form of their salts, that avoid the stated disadvantages and are well suited to use in pharmaceutical-technical formulations and can be processed into these.

A further problem for the present invention is to provide a method for manufacturing such highly pure, crystalline, stable compounds in the form of their salts, as well as highly pure, stable intermediate products.

The final problem for the invention is to provide a method for manufacturing the abovementioned compounds with which a high yield of the products of the process and the respective intermediate products can be obtained chemo- or regioselectively.

This problem is solved in that highly pure, crystalline, stable compounds of the 3,3-diphenylpropylamines in the form of their salts with general formula I are provided,

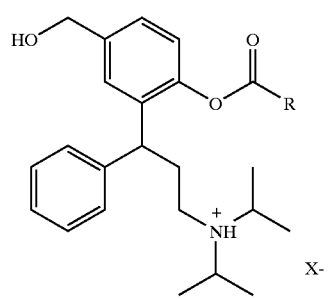

Formula I in which R denotes $C_1$–$C_6$-alkyl, $C_3$–$C_{10}$-cycloalkyl, substituted or unsubstituted phenyl and $X^-$ is the acid residue of a physiologically compatible inorganic or organic acid.

In accordance with a design of the invention the salts of general formula I can contain the respective acid residue $X^-$ of the acids mentioned below:

hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid.

In accordance with a further design form of the invention R-configured compounds with general formula 2 are provided

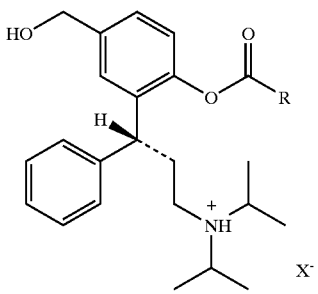

Formula 2 in which R denotes $C_1$–$C_6$-alkyl, $C_3$–$C_{10}$-cycloalkyl, substituted or unsubstituted phenyl and $X^-$ is the acid residue of a physiologically compatible inorganic or organic acid.

In accordance with an advantageous design form of the invention the compounds in the form of their salts of general formula 2 can contain the respective acid residue $X^-$ of the acids mentioned below:

hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid.

Preferred compounds of the present invention are the salts

R-(+)-2-(3-diisopropylamino-1-phenylpropyl)-4-hydroxymethylphenylisobutyrate ester hydrogen fumarate and R-(+)-2-(3-diisopropylamino-1-phenylpropyl)-4-hydroxymethylphenylisobutyrate ester hydrochloride hydrate.

Furthermore, compounds are preferred in which R stands for cyclopropyl, cyclobutyl, cyclopentyl, cyclohexyl, 4-(1-cyclo-propyl-methanoyloxy)-phenyl, 4-(1-cyclobutyl-methanoyloxy)-phenyl, 4-(1-cyclohexyl-methanoyloxy)-phenyl or 4-(2,2-dimethyl-propanoyloxy)-phenyl and X denotes chloride.

Particular preference is for [(R)-3-(2-{1-[4-(1-cyclopropyl-methanoyloxy)-phenyl]-methanoyloxy}-5-hydroxymethyl-phenyl)-3-phenyl-propyl]-diisopropyl-ammonium chloride, [(R)-3-(2-{1-[4-(1-cyclobutyl-methanoyloxy)-phenyl]-methanoyloxy}-5-hydroxymethyl-phenyl)-3-phenyl-propyl]-diisopropyl-ammonium chloride, [(R)-3-(2-{1-[4-(1-cyclohexyl-methanoyloxy)-phenyl]-methanoyloxy}-5-hydroxymethyl-phenyl)-3-phenyl-propyl]-diisopropyl-ammonium chloride, [(R)-3-(2-{1-[4-(2,2-dimethyl-propanoyloxy)-phenyl]-methanoyloxy}-5-hydroxymethyl-phenyl)-3-phenyl-propyl]-diisopropyl-ammonium chloride, {(R)-3-[2-(1-cyclopropyl-methanoyloxy)-5-hydroxymethyl-phenyl]-3-phenyl-propyl}-diisopropyl-ammonium chloride, {(R)-3-[2-(1-cyclobutyl-methanoyloxy)-5-hydroxymethyl-phenyl]-3-phenyl-propyl}-diisopropyl-ammonium chloride, {(R)-3-[2-(1-cyclopentyl-methanoyloxy)-5-hydroxymethyl-phenyl]-3-phenyl-propyl}-diisopropyl-ammonium chloride and {(R)-3-[2-(1-cyclohexyl-methanoyloxy)-5-hydroxymethyl-phenyl]-3-phenyl-propyl}-diisopropyl-ammonium chloride.

In the compounds of the present invention the expression "alkyl" preferably stands for a straight-chain or branched-chain hydrogen group with between 1 and 6 C-atoms. Special preference is for methyl, ethyl, propyl, isopropyl, butyl, isobutyl, pentyl and hexyl. The expression "cycloalkyl" designates cyclical hydrogen groups, that have between 3 and 10 hydrogen atoms, that may also contain suitable substitutes in place of the hydrogen atoms.

The expression "phenyl" designates a —$C_6H_5$-group that may be substituted or unsubstituted. Suitable substitutes can be, for example, alkyl, alkoxy, halogen, nitro and amine. The expression "alkoxy" has, with respect to the alkyl component, the same meaning as already given above for "alkyl". Suitable halogens are fluorine, chlorine, bromine and iodine atoms The present invention also includes methods for manufacturing the compounds in accordance with the invention of general formula I as well as valuable intermediate products.

The method is characterised by chemo- and regioselectivity.

Compounds of General Formula I

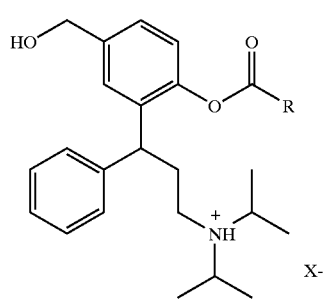

Formula I in which R denotes $C_1$–$C_6$-alkyl, $C_3$–$C_{10}$-cycloalkyl, substituted or unsubstituted phenyl and $X^-$ is the acid residue of a physiologically compatible inorganic or organic acid, are that a) a compound of formula III

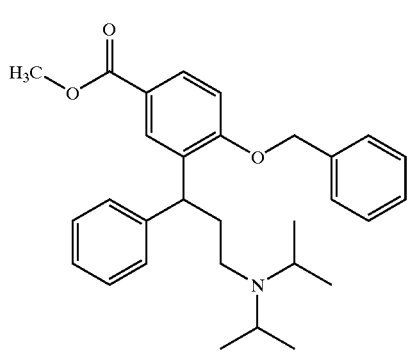

Formula III is split with a hydrogenation agent to form a compound of formula V

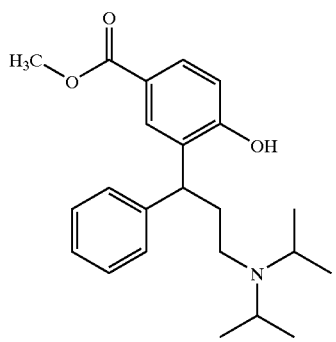

Formula V whereupon b) the compound of formula V so obtained is converted with agent, in order to give a compound of formula VI

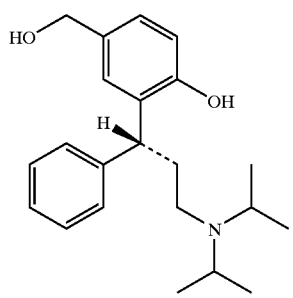

Formula VI which c) is converted with an acylation agent, in order to obtain of formula A

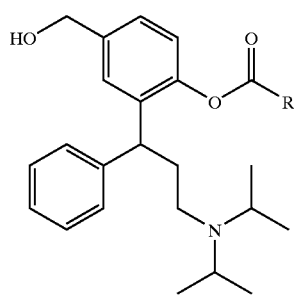

Formula A in which R has the significance stated above, which d) is converted with a physiologically compatible inorganic or organic acid to form a compound of formula I

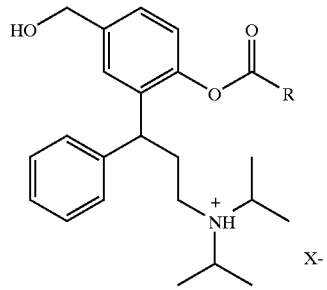

Formula I in which R denotes $C_1$–$C_6$-alkyl, $C_3$–$C_{10}$-cycloalkyl, unsubstituted or substituted phenyl and X– is the acid residue of a physiologically compatible inorganic or organic acid.

In accordance with the invention, for the manufacture of the compounds of general formula I hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid are used.

In accordance with an advantageous further development of the invention a method for the manufacture of R-configured compounds of the general formula 2 is described,

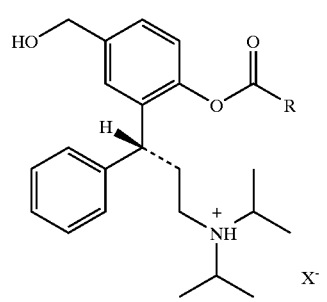

Formula 2 in which R denotes $C_1$–$C_6$-alkyl, $C_3$–$C_{10}$-cycloalkyl, substituted or unsubstituted phenyl and X⁻ is the acid residue of a physiologically compatible inorganic or organic acid, in that a) a compound of formula 3

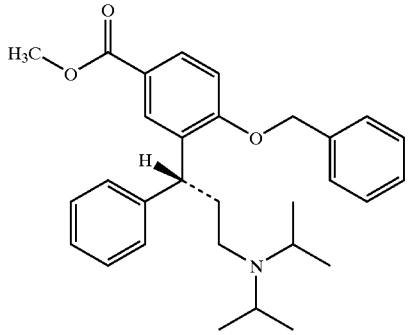

Formula 3 is split with a hydrogenation agent to form a compound of formula 5

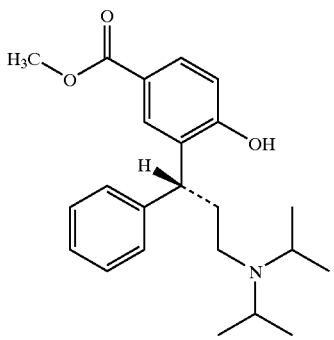

Formula 5 whereupon b) the compound of formula 5 so obtained is converted with a reducing agent, in order to give a compound of formula 6

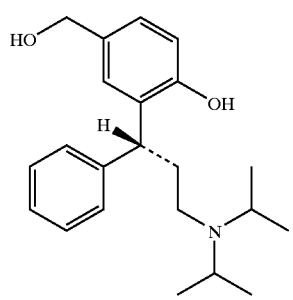

Formula 6 which c) is converted with an acylation agent, in order to obtain a compound of formula 1

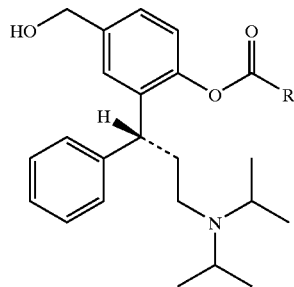

Formula 1 in which R has the significance stated above, which d) is converted with a physiologically compatible inorganic or organic acid to form a compound of formula 2

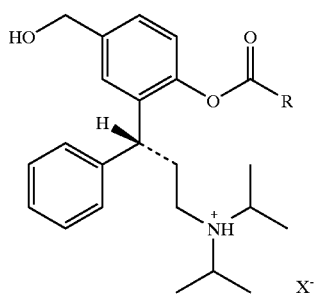

Formula 2 in which R denotes $C_1$–$C_6$-alkyl, $C_3$–$C_{10}$-cycloalkyl, unsubstituted or substituted phenyl and X– is the acid residue of a physiologically compatible inorganic or organic acid.

Advantageously in order to obtain compounds of general formula 2, in accordance with the method hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid are used.

Particular advantageously, on the basis of the crystalline R-(−)-4-benzyloxy-3-(3-diisopropylamino-1-phenyl-propyl)benzoic acid methyl ester, the highly pure, crystalline intermediate product R-(−)-3-(3-diisopropylamino-phenyl-propyl)-4-hydroxy-benzoic acid methyl ester is prepared, which is reduced to R-(+)-2-(3-diisopropylamino-1-phenylpropyl)-4-hydroxymethylphenol, is finally acylated in a suitable manner and is then converted with a physiologically compatible inorganic or organic acid under spontaneous crystallization to the respective highly pure, crystalline, stable salt.

Depending on the acid chloride used, compounds of general formula 1 are obtained, Formula 1

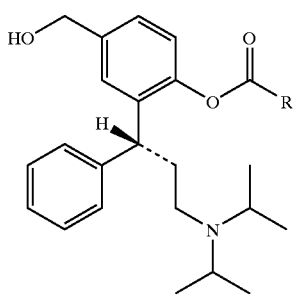

in which R denotes $C_1$–$C_6$-alkyl, in particular isopropyl, $C_3$–$C_{10}$-cycloalkyl or unsubstituted or substituted phenyl.

BRIEF DESCRIPTION OF THE DRAWINGS

In order to obtain the compounds in accordance with the invention in the form of their salts the special reaction process via particular intermediate stages and individually identifiable intermediate products is crucial.

This is explained using reaction diagram 1 (see FIG. 1), in which the conversions with R-configured compounds are described, but without this being restrictive.

Figure 1:
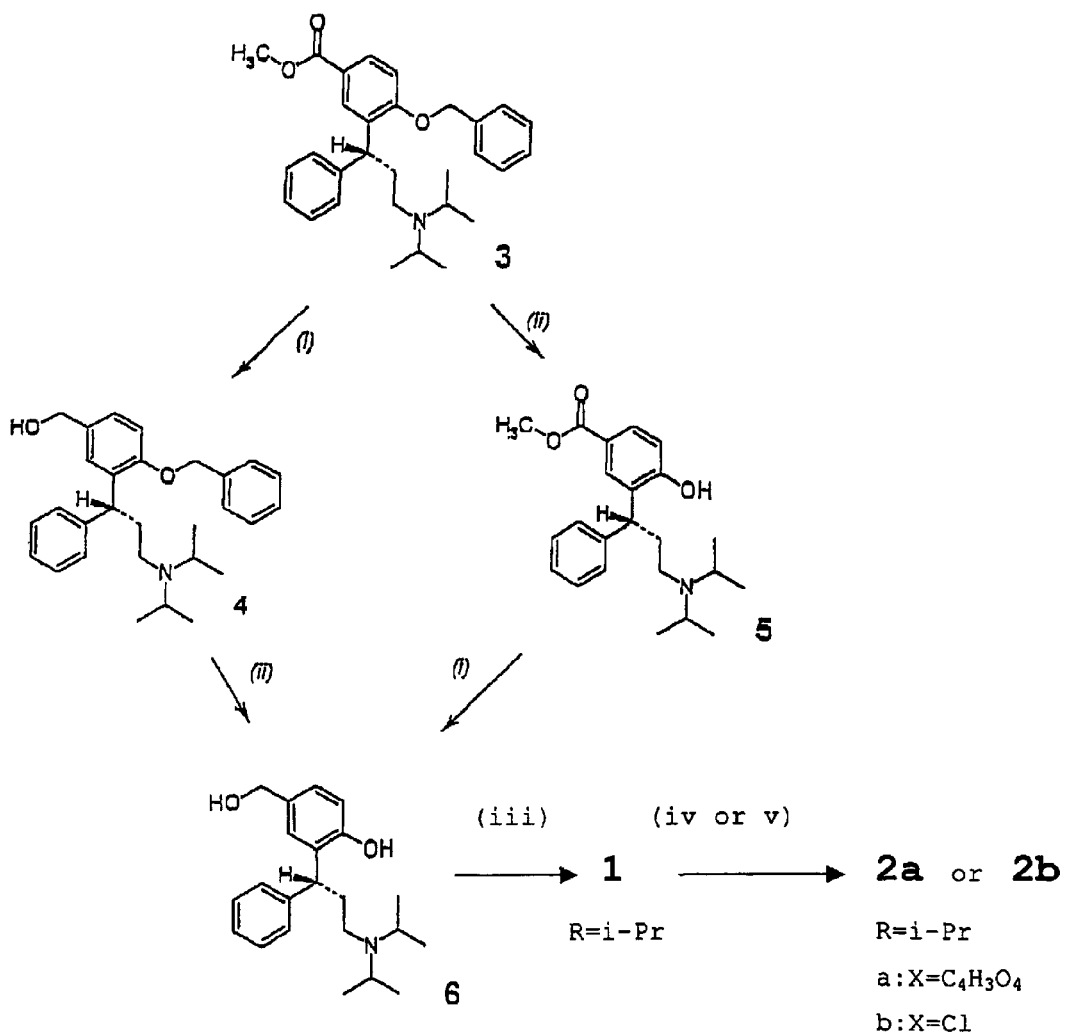

In this:

3=R-(−)-4-benzyloxy-3-(3-diisopropylamino-1-phenyl-propyl)-benzoic acid-methyl ester 4=R-(+)-[4-benzyloxy-3-(3-diisopropylamino-1-phenyl-propyl)-phenyl]-methanol 5=R-(−)-3-(3-diisopropylamino-phenyl-propyl)-4-hydroxy-benzoic acid methyl ester 6=R-(+)-2-(3-diisopropylamino-1-phenylpropyl)-4-hydroxymethylphenol 1=R-(+)-2-(3-diisopropylamino-1-phenylpropyl)-4-hydroxymethylphenyl-isobutyrate ester 2a=R-(+)-2-(3-diisopropylamino-1-phenylpropyl)-4-hydroxymethylphenyl-isobutyrate ester hydrogen fumarate 2b=R-(+)-2-(3-diisopropylamino-1-phenylpropyl)-4-hydroxymethylphenyl-isobutyrate ester hydrochloride hydrate In accordance with the reaction process explained in the embodiment the preliminary stage 3 (R-(−)-4-benzyloxy-3-(3-diisopropylamino-1-phenyl-propyl)-benzoic acid-methylester) is prepared in crystalline, pure form.

Using normal methods—such as $BBr_3$, $AlCl_3$—but preferably by means of hydrogen gas via Raney nickel in methanol as the solvent at room temperature (RT), preliminary stage 3 is split into 5 (R-(−)-3-(3-diisopropylamino-phenyl-propyl)-4-hydroxy-benzoic acid methylester. This develops in highly pure, crystalline form (melting point 143.7° C.).

Finally, using a suitable reducing agent—such as $NaBH_4$/EtOH—preferably $LiAlH_4$ 5 is reduced into an inert solvent at low temperature (−78° C. to +10° C.) and the compound 6 (R-(+)-2-(3-diisopropylamino-1-phenylpropyl)-4-hydroxymethylphenol) is obtained. The compound 6 is obtained in a highly pure state and can be crystallised from a suitable solvent such as ethyl acetate. The colourless, compact grained material has a melting point of 102.3° C. This is surprising in that the compound 6 in the state of the art is described as an amorphous solid.

Compound 6 is now acylated with very good yield and regio- and chemoselectivity, into a phenolic ester. This reaction is performed at RT or low temperatures with an equivalent acid chloride in the presence of a base in a suitable solvent. Suitable solvents are ethyl acetate, dichloromethane, tetrahydrofurane, acetonitrile or toluene.

The reaction is preferably performed with isobutyrylchloride as the acid chloride and triethylamine as the base at the abovementioned temperatures. The 1 (R-(+)-2-(3-diisopropylamino-1-phenylpropyl)-4-hydroxymethylphenylisobutyrate ester) then obtained, occurs with such purity that with solutions of the fumaric acid in suitable solvents spontaneous crystallisation starts with the formation of the hydrogen fumarate salt 2a.

This salt has a high melting point of 103° C., is stable at RT, is non-hygroscopic and does not contain crystallose agents. It can be recrystallised as often as desired.

If instead of fumaric acid anhydrous hydrochloric acid is used—for example as an etheric solution—salt formation also takes place with the crystalline product 2b (R-(+)-2-(3-diisopropylamino-1-phenylpropyl)-4-hydroxymethylphenyl-isobutyrate ester hydrochloride hydrate being obtained.

Following a further recrystallisation the product 2b has a melting point range of 97–106° C.

Finally the product 2b can particularly advantageously be obtained by the following variants of the inverse reaction process, starting with the compound 6 of reaction diagram 1. The product 2b can thus be obtained without the addition of an external acid-intercepting base, as explained in the following.

Solutions of 6 (R-(+)-2-(3-diisopropylamino-1-phenylpropyl)-4-hydroxymethylphenol) are dripped into solutions of isobutyrate chloride, so that under suitable polarity conditions the anhydrous product 2b rapidly crystallises out. 2b is very hygroscopic.

If the abovementioned reaction is carried out in a humid solvent, that contains at least one mole equivalent of water, a stable and crystalline, hydrate-containing product 2b is obtained, that has the abovementioned melting characteristics.

The compounds in accordance with the invention of general formulae 1 and 2 are suited to bulk material.

Of particular advantage are the highly pure compounds of general formulas III, V, VI, 3, 5, 6 and 7 which can be obtained.

Compound of Formula III

Formula III

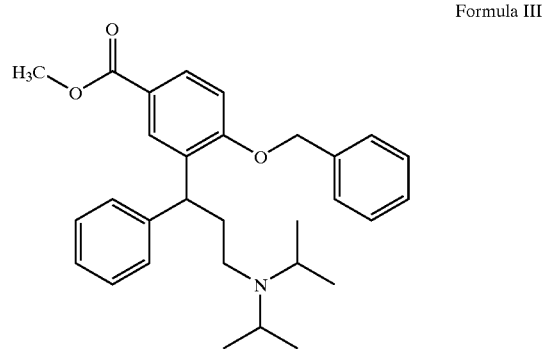

Compound of Formula V

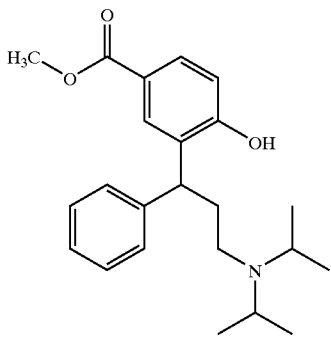

Compound of Formula VI

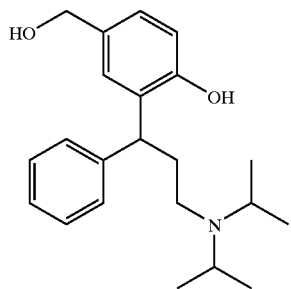

Compound of Formula 3

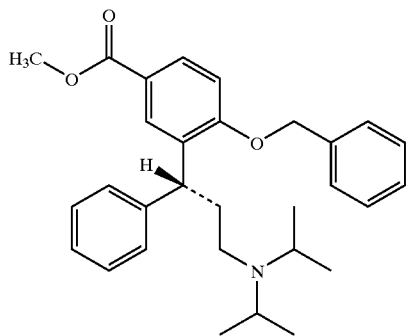

Compound of Formula 5

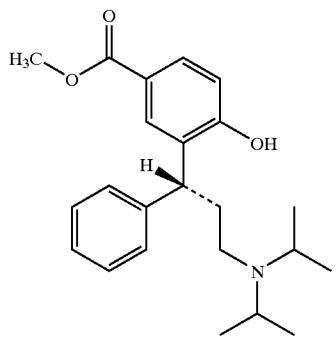

Compound of formula 6

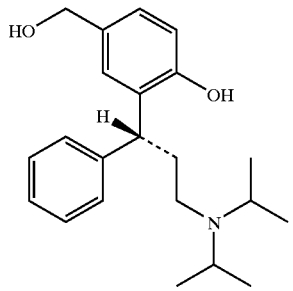

Compound of Formula 7

[(R)-3-(2-{1-[4-(2,2-dimethyl-propanoyloxy)-phenyl]-methane-oyloxy}-5-{1-[4-(2,2-dimethyl-propanoyloxy)-phenyl]-methane-oyloxymethyl}-phenyl)-3-phenyl-propyl]-diisopropyl-ammonium-chloride.

The abovementioned compounds III, V, VI, 3, 5, 6 and 7 are particularly suited to use in each case as a highly pure, crystalline, stable intermediate product in the manufacture of pharmaceutically useful compounds.

Of particular advantage are compounds for use as an intermediate product in the manufacture of R-(+)-2-(3-diisopropylamino-1-phenylpropyl)-4-hydroxymethylphenylisobutyrate ester hydrogen fumarate and R-(+)-2-(3-diisopropylamino-1-phenylpropyl)-4-hydroxymethylphenylisobutyrate ester hydrochloride hydrate.

Finally, the method can be carried out in a particularly advantageous way by converting a compound of general formula 6 (see reaction diagram 1) with an equivalent isobutyryl chloride in the presence of triethylamine using one of the respective solvents ethylacetate, dichloromethane, tetrahydrofurane, acetonitrile or toluene regio- and chemoselectively into R-(+)-2-(3-diisopropylamino-1-phenylpropyl)-4-hydroxymethylphenylisobutyrate ester.

In accordance with the invention R-(+)-2-(3-diisopropylamino-1-phenylpropyl)-4-hydroxymethylphenylisobutyrate ester is particularly suited to conversion with fumaric acid or hydrochloric acid with the formation of the respective salt.

The following embodiments explain the invention.

Experimental

I. General

All compounds have been fully characterised by $^1$H and $^{13}$C NMR-spectroscopy (Bruker DPX 200). The stated chemical displacements in the $^{13}$C-NMR-spectra (50 MHz, ppm values stated) refer to the solvent resonances of CDCl$_3$ (77.10 ppm) $^1$H NMR data (CDCl$_3$; 200 MHz, ppm) refer to internal tetramethylsilane).

Thin layer chromatography (DC, $R_f$ given) was carried out on 5×10 cm E. Merck silica gel films (60F254), and the stains were revealed by fluorescence erasure or by spraying with alkaline potassium permanganate solution.

Absorbent systems were: (1), n-hexane/acetone/triethylamine (70/20/10, v/v-%); (2), toluene/acetone/methanol/acetic acid (70/5/20/5, v/v-%).

The optical rotations were measured at a wavelength of 589.3 nm (sodium D-line), at room temperature using ethanol as a solvent (apparatus: Perkin Elmer Polarimeter Type 241), melting points (in ° C.) are uncorrected and were determined on the Mettler FP apparatus, or by differential thermoanalysis (DSC) on the Perkin Elmer Model DSC7, using "Pyris" evaluation software.

UV/VIS measurements were carried out on the spectrophotometer. model Lambda 7 (Perkin-Elmer) with a layer thickness of 1 cm. The specific absorption stated is for a 1% solution ($A^1 \%_{1\ cm}$)

IR spectra were recorded on a Perkin-Elmer FTIR spectrometer Series 1610 (resolution 4 $cm^{-1}$).

Gas chromatography mass spectrometry (GC-MS, m/z values and relative intensity with reference to the base ion (%) was carried out with a Finnigan TSQ 700 Triple Mass Spectrometer in positive (P-CI) or negative (N-CI) chemical ionization measurement mode with methane or ammonium as a reactant gas or via electron impact ionisation. Hydroxy compounds were measured as trimethylsilylether-derivatives.

Coupled liquid chromatography-mass spectrometry (LC-MS): Waters Integrity System, Thermabeam Mass Detector (EI, 70 eV), m/z-values and relative intensity (%) are given over a quantity range of 50–500 a.m.u.

II. Embodiments

The Arabic numerals in brackets (3), (4), (5), (6) refer to the identical designations in reaction diagram 1.

1. Preparation of R-(−)-4-benzyloxy-3-(3-diisopropylamino-1-phenyl-propyl)-benzoic acid methyl-ester (3)

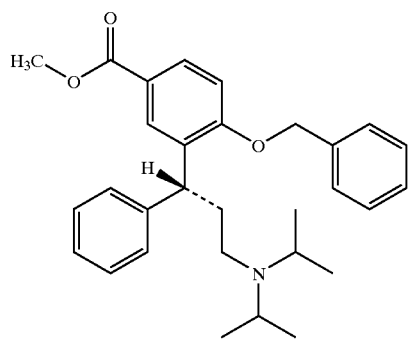

A solution of R-(−)-4-benzyloxy-3-(3-diisopropylamino-1-phenyl-propyl)-benzoic acid hydrochloride (2.30 kg, 4.77 Mol) in 26.4 litres of methanol and 0.25 litre of concentrated sulphuric acid is heated for 16 hours with recycling. Then a third of the solvent is distilled off, cooled and under agitation mixed with 5 kg ice and 2.5 litres 25% aqueous sodium carbonate solution. The deposit is first extracted with 15 litres and then again with 5 litres of dichloromethane. The organic phases are purified and concentrated on the rotary evaporator until dry. 1.99 kg (90.7% of theoretical) dark yellow oil with a purity of approximately 90% (DC, NMR) are obtained.

DC (1): 0.58

$^{13}$C-NMR (CDCl$_3$): 20.55, 20.65, 36.83, 41.84, 43.63, 51.82, 70.12, 111.09, 122.46, 125.28, 127.49, 128.02, 128.35, 128.50, 129.22, 129.49, 133.20, 136.39, 144.51, 159.87, 167.09.

Recrystallisation 69.0 oily raw material is dissolved in 150 ml boiling methanol. Following the addition of 15 ml distilled water it is left at 0° C., whereupon colourless crystals precipitate. These are filtered off, washed with a little cold methanol and vacuum-dried. Yield: 41.8 g (60.6% of theoretical) colourless crystals, melting point 89.8° C.; $[I]_D^{20}$=−30.7(c=1.0, ethanol).

2. Preparation of R-(+)-[4-benzyloxy-3-(3-diisopropylamino-1-phenyl-propyl)-phenyl]-methanol (4)

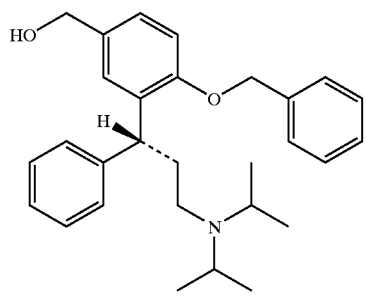

Raw product (3) (28 g) is dissolved in 230 ml pure diethylether and under agitation is dripped into a suspension of 1.8 g lithium-aluminium hydride in diethylether (140 ml). After 18 hours of agitation at room temperature, 4.7 ml of water are added in drop form. The organic phase is separated off, dried with anhydrous sodium sulphate, filtered and concentrated on the rotary evaporator until dry. 26 g (98.9% of theoretical) R-(+)-[4-benzyloxy-3-(3-diisopropylamino-1-phenyl-propyl)-phenyl]-methanol (4) are obtained as a colourless oil.

DC (2): 0.32; $[I]_D^{20}$=+6.3 (c=1.0, ethanol).

$^{13}$C-NMR (CDCl$_3$): 20.53, 20.61, 36.87, 41.65, 44.14, 48.82, 65.12, 70.09, 111.80, 125.77, 125.97, 126.94, 127.55, 128.08, 128.37, 128.44, 133.27, 134.05, 134.27, 137.21, 144.84.

3. Preparation of R-(−)-3-(3-diisopropylamino-phenyl-propyl)-4-hydroxy-benzoic acid methyl ester (5)

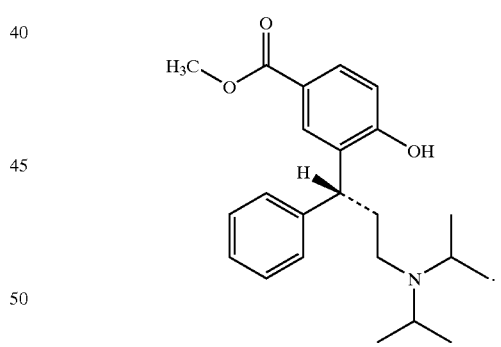

To an agitated suspension of 5 g Raney nickel (washed with water, then with methanol) in 200 ml methanol, 10 g (21.8 mmol) R-(−)-4-benzyloxy-3-(3-diisopropylamino-1-phenyl-propyl)-benzoic acid methyl ester (3) are added. Following brief heating, in order to dissolve all (3) completely, the apparatus is placed under a hydrogen gas atmosphere. After three hours of agitation at normal pressure and room temperature, the thin layer chromatography demonstrates complete conversion. The deposit is rinsed with nitrogen gas and following addition of some active charcoal is filtered. Following concentration of the methanolic solution on the rotary evaporator 6.0 g (75% of theoretical) R-(−)-3-(3-diisopropylaminophenyl-propyl)-4-hydroxy-benzoic acid methyl ester (5) remains in the form of colourless crystals with a purity of 99.6% (HPLC).

Melting point 143.7° C.; DSC 144.7° C.
$[I]_D^{20} = -26.6$ (c=0.93, ethanol).
$^{13}$C-NMR (CDCl$_3$): 18.74, 19.21, 19.62, 33.12, 39.68, 42.36, 48.64, 51.42, 117.99, 120.32, 126.23, 127.81, 128.85, 129.39, 130.26, 132.21, 144.06, 162.43, 167.35.

4. Preparation of R-(+)-2-(3-diisopropylamino-1-phenylpropyl)-4-hydroxymethylphenol (6)

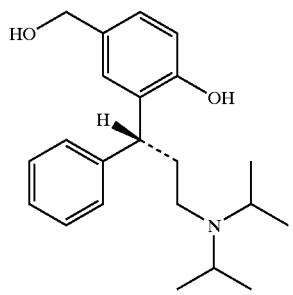

a) Starting from the intermediate stage (4), R-(+)-[4-benzyloxy-3-(3-diisopropylamino-1-phenyl-propyl)-phenyl]-methanol R-(+)-[4-benzyloxy-3-(3-diisopropylamino-1-phenyl-propyl)-phenyl]-methanol (19.7 g, 45.7 mmol) are dissolved in 220 ml methanol and Raney nickel (5 g). The apparatus is rinsed with hydrogen gas and the deposit is agitated for two days at room temperature. Following the addition of a further 5 g Raney nickel, agitation for a further two days at room temperature takes place under a hydrogen gas atmosphere, followed by filtration off from the catalyser and concentration until dry on the rotary evaporator. The oily, pale yellow residue is dissolved in 100 ml diethylether, washed twice with 100 ml water each time, dried via sodium sulphate, filtered and concentrated until dry. 14.1 g (90.4% of theoretical) R-(+)-2-(3-diisopropylamino-1-phenylpropyl)-4-hydroxymethylphenol are obtained in the form of a cream-coloured, amorphous. solid. For recrystallisation see under c).

b) Starting from the intermediate stage (5); R-(−)-3-(3-diisopropylamino-phenyl-propyl)-4-hydroxy-benzoic acid methyl ester A solution of 370 mg (1.0 mmol) R-(−)-3-(3-diisopropylamino-phenyl-propyl)-4-hydroxy-benzoic acid methyl ester in 20 ml anhydrous tetrahydrofurane is slowly and at room temperature dropped into an agitated mixture of dried tetrahydrofurane (10 ml) and a 1M solution of lithium-aluminium hydride in tetrahydrofurane (3 ml) (under a nitrogen protective gas atmosphere). Excess hydride is decomposed by the dropped addition of a saturated sodium carbonate solution. Following separation of the organic phase this is concentrated on the rotary evaporator and then dried in the high-vacuum. 274 mg (74% of theoretical) pale yellow oil is obtained, that slowly solidifies into an amorphous mass.

c) Recrystallisation

Raw product 6 (1.0 g) is dissolved in ethyl acetate and again concentrated on the rotary evaporator. The diol released in this way from foreign solvents (diethyl ether or tetrahydrofurane, see above) has 1.5 ml ethyl acetate added with slight heating. Agitation takes place until a clear solution results, followed by cooling at room temperature and addition of a few seed crystals. These are obtained by purifying raw 6 via HPLC, collecting the main fraction, concentrating this and drying the residue for a number of hours in the high-vacuum. Once clear crystallisation has definitely started, it is left at −10° C. The crystals are sucked off in the cold and dried in the vacuum. Colourless crystals with a yield of 84% are obtained.

Melting point 102.3° C.
DC (1): 0.57
$[I]_D^{20} = +21.3$ (c=1.0, ethanol).
$^{13}$C-NMR (CDCl$_3$): 19.58, 19.96, 33.30, 39.52, 42.10, 48.00, 65.40, 118.58, 126.31, 126.57, 127.16, 127.54, 128.57, 132.63, 132.83, 144.55, 155.52.

5. Preparation of R-(+)-2-(3-diisopropylamino-1-phenylpropyl)-4-hydroxymethylphenolisobutyrate ester (1)

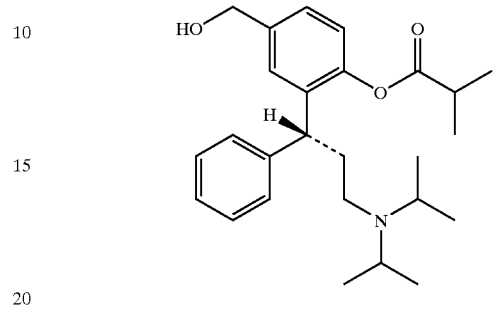

A solution of R-(+)-2-(3-diisopropylamino-1-phenylpropyl)-4-hydroxymethylphenol (6) (65.0 g, 190.3 mmol) and triethylamine (20.4 g, 201.7 mmol) in 750 ml dichloromethane has a solution of isobutyrate chloride (23.4 g, 201.7 mmol) in 250 ml dichloromethane added under agitation and cooling. Following addition agitation takes place for a further 15 minutes at 0° C., then for 30 minutes at room temperature and then one after another washing with water (250 ml) and 5% aqueous sodium hydrogen carbonate solution. The organic phase is separated and concentrated on the rotary evaporator until dry. The ester R-(+)-2-(3-diisopropylamino-1-phenylpropyl)-4-hydroxymethylphenylisobutyrate ester is obtained as a colourless, viscous oil; yield: 77.1 g (98.4% of theoretical).

DC (1): 0.26; $[I]_D^{22} = +2.7$ (c=1.0, ethanol).
$^{13}$C-NMR (CDCl$_3$): 19.01, 19.95, 20.59, 21.12, 34.28, 36.89, 41.88, 42.32, 43.90, 48.78, 64.68, 122.57, 125:59, 126.16, 126.86, 127.96, 128.54, 136.88, 138.82, 143.92, 147.90, 175.96.

6. Preparation of R-(+)-2-(3-Diisopropylamino-1-phenylpropyl)-4-hydroxymethyl-phenylisobutyrate ester hydrogen fumarate.

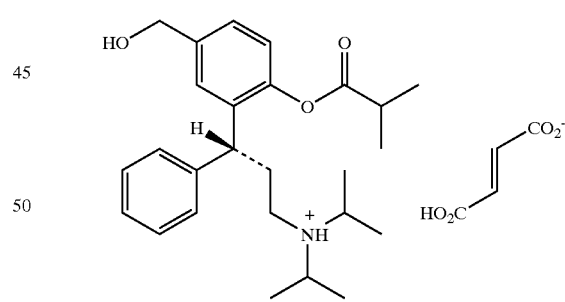

A solution of 41.87 g (102 mmol) R-(+)-2-(3-diisopropylamino-1-phenylpropyl)-4-hydroxymethylphenylisobutyrate ester in 90 ml 2-butanone has fumaric acid (11.81 g, 102 mmol) added while heating. Following dissolution of the acid, cyclohexane (20–30 ml) is slowly added under agitation until the onset of turbidity. The colourless, homogenous deposit is initially left for 18 hours at room temperature, and then for several hours at 0° C. The colourless crystals that have precipitated are sucked off, washed with a little cyclohexane/2-butanone (90:10, vol.-%)and dried in the vacuum at 30° C. 44.6 g (83.1% of theoretical) hydrogen furate salt of R-(+)-2-(3-diisopropylamino-1-phenylpropyl)-4- hydroxymethylphenyl-isobutyrate ester in the form of colourless flakes are obtained.

Melting point 98.8° C., a second crystallisation from the same solvent mixture provides a product with a melting point of 103° C.

$[I]_D^{20}=+6.0$ (c=1.0, ethanol).

Elementary analysis: Calculated for $C_{30}H_{41}NO_7$ (molecular weight 527.66) C 68.29%, H 7.83%, N 2.65%, O 21.2%; found C, 68.29%; H, 7.90%; N, 2.72%; O, 21.0%.

UV/VIS at Σ in nm ($A^1 \%_{1\ cm}$): 191 (1306), 193 (1305), 200 (1143), 220 (456).

IR: 3380, 2978, 2939, 2878, 2692, 2514, 1756, 1702, 1680, 1618, 1496, 1468, 1226, 1040, 1019, 806, $^1$H-NMR (CDCl$_3$): 1.198, 1.285, 1.287 (CH$_3$); 2.541 (CHC=O); 3.589 (NCH); 4.585 (CH$_2$OH); 6.832 (=CH, fumarate); 6.84–7.62 (aryl, =CH).

$^{13}$C-NMR (CDCl$_3$): 17.79, 18.95, 19.16 (CH$_3$); 31.63 (CHCH$_2$); 34.09 (CH—C=O); 41.87 (CHCH$_2$); 45.83 (NCH$_2$); 54.29 (NCH); 63.78 (OCH$_2$); 122.23, 126.48, 126.77, 127.56, 140.46, 140.52, 142.35, 147.54 (Aryl CH); 135.54 (=CH, fumarate); 170.48 (C=O, fumarate); 175.62 (i-Pr—C=O).

Ms in the direct inlet, m/z (%): 411 (1), 396 (9), 380 (1), 223 (2), 165 (2), 114 (100), 98 (4), 91 (3), 84 (3), 72 (10), 56 (7).

7. Preparation of R-(+)-2-(3-Diisopropylamino-1-phenylpropyl)-4-hydroxymethyl-phenylisobutyrate ester hydrochloride hydrate

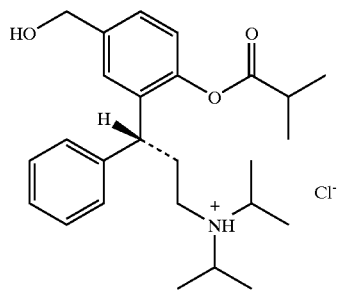

A solution of R-(+)-2-(3-diisopropylamino-1-phenylpropyl)-4-hydroxymethylphenylisobutyrate ester (8.54 g, 25.0 mmol) in 50 ml dichloromethane is slowly dropped at 0° C. into an agitated solution of isobutyrate chloride (2.66 g, 25.0 mmol) in 100 ml dichloromethane. After an hour the cooling is removed and re-agitation takes place for an additional hour. Following the drawing off of the volatile components in the vacuum on the rotary evaporator a colourless, amorphous-solid foam remains. This residue is dissolved in acetone (17 ml), with 0.45 to 0.50 g water and diethyl ether is added (approx. 20–25 ml) until there is a definite onset of turbidity. Following brief treatment with ultrasound crystallisation starts spontaneously and under agitation a further 80 ml of diethyl ether are slowly added. The precipitated colourless crystals are sucked off and dried overnight in the vacuum via phosphorous pentoxide. 10.5 g (93.7% of theoretical) colourless crystalline R-(+)-2-(3-diisopropylamino-1-phenylpropyl)-4-hydroxymethylphenylisobutyrate ester hydrochloride hydrate with a purity of 97.0% (HPLC) are obtained.

Melting point 97.1° C.

$[I]_D^{20}=+4.3$ (c=1.03, ethanol)

$^{13}$C-NMR (CDCl$_3$): 16.94, 17.35, 18.24, 18.40, 18.87, 19.05, 31.20, 33.99, 41.64, 45.41, 54.18, 54.42, 63.83, 122.25, 126.50, 126.70, 126.96, 127.34, 128.60, 133.80, 140.55, 142.17, 147.68, 175.79.

8. Phenolic Monoester

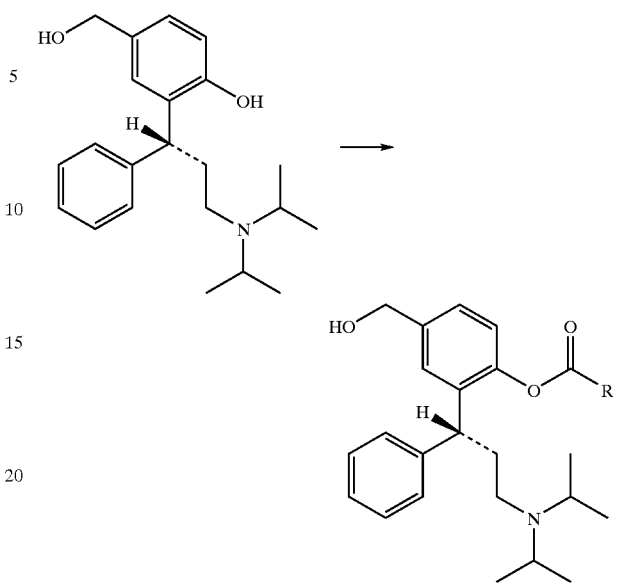

General Work Specification for the Manufacture of Phenolic Monoesters

Into a solution of 120.3 mg (0.352 mmol)R-(+)-2-(3-diisopropylamino-1-phenylpropyl)-4-hydroxyphenol (6) in 5 ml dichloromethane, under agitation at 0° C., a solution of acid chloride (0.352 mmol) in 2 ml dichloromethane is dropped. Then triethylamine-dichloromethane (49.1 μl/0.353 mmol-2 ml) is added. After 18 hours at room temperature the thin layer chromatography shows that conversion is complete. The deposit is washed successively with 5 ml water, aqueous 0.1N-hydrochloric acid, 5 ml 5% aqueous sodium-hydrogen carbonate solution, 5 ml water, dried via sodium sulphate and following filtration concentrated until dry. Then it is dried in the high-vacuum until constant weight.

The following compounds are, by way of example, manufactured using this method:

R=CH$_2$CH (CH$_3$)$_2$

R-(+)-3-methylbutyric acid-2-(3-diisopropylamino-1-phenyl-propyl)-4-hydroxymethylphenyl-ester Colourless oil with 70% yield and >95% purity (NMR).

$^{13}$C-NMR (CDCl$_3$): 20.45, 20.59, 22.54, 25.70, 36,74, 42.18, 43.27, 43.96, 48.90, 64.67, 122.66, 125.60, 126.20, 126.79, 127.95, 128.37, 136.83, 138.86, 143.83, 147.82, 171.37.

DC (1): 0.76.

R=CH$_2$C(CH$_3$)$_3$

R-(+)-3.3-dimethylbutyric acid-2-(3-diisopropylamino-1-phenyl-propyl)-4-hydroxymethylphenyl-ester, free base Colourless oil with 69.7% yield and >95% purity (NMR).

$^{13}$C-NMR (CDCl$_3$): 20.40, 20.53, 29.73, 30.99, 36.62, 42.17, 44.01, 47.60, 49.01, 64.65, 122.64, 125.60, 126.20, 126.80, 127.96, 128.36, 136.85, 138.90, 143.80, 147.82, 170.55.

DC (1): 0.75.

R=(CH$_3$)$_3$C

R-(+)-3-pivalic acid-2-(3-diisopropylamino-1-phenyl-propyl)-4-hydroxymethylphenyl-ester hydrochloride.

Colourless crystals, melting point 165–6° C.

$^{13}$C-NMR (DMSO-d$_6$=39.7 ppm): 16.52, 16.68, 17.98, 18.11, 26.87, 31.46, 41.71, 45.33, 53.89, 53.98, 62.65, 122.61, 122.97, 125.94, 126.09, 126.57, 126.75, 127.87, 128.58, 131.80, 134.94, 141.02, 142.69, 147.17, 155.32, 163.92, 176.21.

R=c-C$_3$H$_5$
R-(+)-cyclopropane carboxylic acid-2-(3-diisopropylamino-1-phenyl-propyl)-4-hydroxymethylphenyl-ester hydrochloride.

Colourless, waxy substance.

$^{13}$C-NMR (DMSO-d$_6$=39.7 ppm): 173.02, 172.49, 172.37, 153.10, 147.12, 142.72, 142.03, 140.78, 136.60, 134.79, 134.35, 129.55, 129.13, 128.80, 128.67, 127.87, 126.96, 126.74, 125.94, 125.84, 124.37, 123.71, 122.80, 62.64, 53.92, 45.34, 41.65, 31.44, 18.05, 16.66, 12.84, 9.58, 9.28, 8.49, 7.89.

R=c-C$_4$H$_7$
R-(+)-cyclobutane carboxylic acid-2-(3-diisopropylamino-1-phenyl-propyl)-4-hydroxymethylphenyl-ester hydrochloride Colourless, waxy substance.

$^{13}$C-NMR (DMSO-d$_6$=39.7 ppm): 173.53, 147.12, 142.81, 140.74, 134.77, 128.65, 127.81, 126.74, 125.99, 125.87, 122.75, 62.63, 53.92, 45.34, 41.42, 37.38, 31.54, 25.04, 24.92, 18.03, 16.68, 16.61.

R=c-C$_5$H$_9$
R-(+)-cyclopentane carboxylic acid-2-(3-diisopropylamino-1-phenyl-propyl)-4-hydroxymethylphenyl-ester hydrochloride Colourless, waxy substance.

$^{13}$C-NMR (DMSO-d$_6$=39.7 ppm): 174.80, 147.22, 142.86, 140.76, 134.72, 128.66, 127.80, 126.73, 126.04, 125.88, 122.71, 62.62, 53.94, 45.37, 43.24, 41.39, 31.54, 29.78, 29.59, 25.64, 25.59, 18.07, 16.64.

R=c-C$_6$H$_{11}$
R-(+)-cyclohexane carboxylic acid-2-(3-diisopropylamino-1-phenyl-propyl)-4-hydroxymethylphenyl-ester hydrochloride Colourless, waxy substance.

$^{13}$C-NMR (DMSO-d$_6$=39.7 ppm): 174.08, 147.15, 142.85, 140.77, 134.78, 128.66, 127.77, 126.74, 126.06, 125.87, 122.69, 62.61, 53.91, 45.36, 42.26, 41.24, 31.53, 28.74, 28.62, 25.48, 25.04, 24.98, 18.05, 16.67, 16.60.

R=4-(C$_2$H$_5$CO$_2$)-C$_6$H$_4$
R-(+)-4-ethylcarbonyloxy-benzoic acid-2-(3-diisopropylamino-1-phenyl-propyl)-4-hydroxymethylphenyl-ester hydrochloride Colourless crystals, melting point 195–8° C.

$^1$H-NMR (DMSO-d$_6$): 9.87 (s, 1H can be substituted with D$_2$O, NH), 8.19–8.12 (m, 2H, Phenyl-H), 7.55 (d, J=1.0 Hz, 1H, Phenyl-H3), 7.41–7.13 (m, 9H, Phenyl-H), 5.28 (br s, 1H can be substituted with D$_2$O, OH), 4.53 (s, 2H, CH$_2$), 4.23 (t, J=7.6 Hz, 1H, CH), 3.61–3.50 (m, 2H, 2×CH(CH$_3$)$_2$), 2.97–2.74 (m, 2H, CH$_2$), 2.67 (q, J=7.4 Hz, 2H, CH$_2$), 2.56–2.43 (m, 2H, CH$_2$), 1.23–1.13 (m, 15H, 2×CH(CH$_3$)$_2$, CH$_3$).

R=4-(i-C$_3$H$_7$CO$_2$)—C$_6$H$_4$
R-(+)-4-(isopropylcarbonyloxy)-benzoic acid-2-(3-diisopropylamino-1-phenyl-propyl)-4-hydroxymethylphenyl-ester hydrochloride Colourless crystals, melting point 202–4° C.

$^1$H-NMR (DMSO-d$_6$): 9.73 (s, 1H can be substituted with D$_2$O, NH), 8.19–8.12 (m, 2H, Phenyl-H), 7.55 (d, J=1.4 Hz, 1H, Phenyl-H3), 7.42–7.14 (m, 9H, Phenyl-H), 5.27 (br s, 1H can be substituted with D$_2$O, OH), 4.53 (s, 2H, CH$_2$), 4.23 (t, J=7.5 Hz, 1H, CH), 3.61–3.50 (m, 2H, 2×CH(CH$_3$)$_2$), 2.99–2.78 (m, 3H, CH$_2$, CH(CH$_3$)$_2$), 2.54–2.47 (m, 2H, CH$_2$), 1.29–1.13 (m, 18H, 3×CH(CH$_3$)$_2$)

R=4-(t-C$_4$H$_9$CO$_2$)—C$_6$H$_4$
R-(+)-4-(t-butylcarbonyloxy)-benzoic acid-2-(3-diisopropylamino-1-phenyl-propyl)-4-hydroxymethylphenyl-ester, free base.

Colourless oil.

$^1$H-NMR (DMSO-d$_6$): 8.19–8.12 (m, 2H, phenyl-H), 7.45–7.33 (m, 3H, phenyl-H), 7.25–7.09 (m, 7H, phenyl-H), 5.20 (t, J=5.6 Hz, 1H, OH), 4.50 (d, J=5.6 Hz, 2H, CH$_2$), 4.20 (t, J=7.5 Hz, 1H, CH), 2.95–2.80 (m, 2H, 2×CH(CH$_3$)$_2$), 2.38–2.25 (m, 2H, CH$_2$), 2.09–2.03 (m, 2H, CH$_2$), 1.33 (s, 9H, (CH$_3$)$_3$), 0.82–0.76 (m, 12H, 2×CH(CH$_3$)$_2$).

Hydrochloride: colourless crystals, melting point 165–6° C.

$^1$H-NMR (CDCl$_3$): 8.22–8.16 (m, 2H, phenyl-H), 8.02 (d, J=1.8 Hz, 1H, phenyl-H), 7.27–7.02 (m, 9H, phenyl-H), 4.83–4.60 ('m', 2H, CH$_2$), 4.01–3.94 (m, 1H, CH), 3.66–3.54 (m, 2H), 3.18–2.80 (m, 3H), 2.53–2.44 (m, 1H) (2×CH$_2$, 2×CH(CH$_3$)$_2$), 1.43–1.25 (m, 21H, (CH$_3$)$_3$, 2×CH(CH$_3$)$_2$).

R=4-(c-C$_3$H$_5$CO$_2$)-C$_6$H$_4$
R-(+)-4-(cyclopropylcarbonyloxy)-benzoic acid-2-(3-diisopropylamino-1-phenyl-propyl)-4-hydroxymethylphenyl-ester hydrochloride Colourless crystals, melting point 208–213° C.

$^1$H-NMR (DMSO-d$_6$): 9.04 (s, 1H can be substituted with D$_2$O, NH), 8.15–8.09 (m, 2H, phenyl-H), 7.53 ('d', 1H, phenyl-H3), 7.42–7.13 (m, 9H, phenyl-H), 5.25 (br s, 1H can be substituted with D$_2$O, OH), 4.52 (s, 2H, CH2), 4.23 (t, J=7.5 Hz, 1H, CH), 3.62–3.53 (m, 2H, 2×CH(CH3)2), 3.05–2.70 (m, 2H, CH2), 2.51–2.37 (m, 2H, CH2), 2.01–1.89 (m, 1H, cyclopropyl-CH), 1.20–1.05 (m, 16H, 2×CH(CH3)2, 2×cyclopropyl-CH2).

$^{13}$C-NMR (DMSO-d$_6$=39.7 ppm): 172.71, 163.93, 154.92, 147.16, 142.69, 141.03, 134.97, 131.76, 128.60, 127.86, 126.76, 126.56, 126.06, 125.94, 122.95, 122.65, 62.65, 54.00, 53.89, 45.33, 41.63, 31.49, 18.10, 17.98, 16.69, 16.51, 12.86, 9.52.

R=4-(c-C$_4$H$_7$CO$_2$)-C$_6$H$_4$
R-(+)-4-(cyclobutylcarbonyloxy)-benzoic acid-2-(3-diisopropylamino-1-phenyl-propyl)-4-hydroxymethylphenyl-ester hydrochloride Colourless crystals, melting point 201–6° C.

$^1$H-NMR (DMSO-d$_6$): 9.50 (s, 1H can be substituted with D$_2$O, NH), 8.17–8.12 (m, 2H, phenyl-H), 7.54 (d, J=1.4 Hz, 1H, phenyl-H3), 7.42–7.14 (m, 9H, phenyl-H), 5.25 (br s, 1H can be substituted with D$_2$O, OH), 4.52 (s, 2H, CH$_2$), 4.23 (t, J=7.5 Hz, 1H, CH), 3.62–3.47 (m, 3H, cyclobutyl-CH), 2×CH(CH$_3$)$_2$), 3.00–2.70 (m, 2H, CH$_2$), 2.51–2.26 (m, 6H, CH$_2$, 2×cyclobutyl-CH$_2$), 2.10–1.85 (m, 2H, cyclobutyl-CH$_2$), 1.22–1.12 (m, 12H, 2×CH(CH$_3$)$_2$).

R=4-(c-C$_6$H$_{11}$CO$_2$)-C$_6$H$_4$
R-(+)-4-(cyclohexylcarbonyloxy)-benzoic acid-2-(3-diisopropylamino-1-phenyl-propyl)-4-hydroxymethylphenyl-ester hydrochloride Colourless crystals, melting point 212–217° C.

$^1$H-NMR (DMSO-d$_6$): 9.34 (s, 1H, can be substituted with D$_2$O, NH), 8.16–8.12 (m, 2H, phenyl-H), 7.54 (d, J=1.4 Hz, 1H, phenyl-H3), 7.39–7.14 (m, 9H, Phenyl-H), 5.26 ('t', 1H, can be substituted with D$_2$O), 4.53 (d, J=4.2 Hz, 2H, CH$_2$), 4.22 (t, J=7.5 Hz, 1H, CH), 3.62–3.48 (m, 2H, 2×CH(CH$_3$)$_2$), 3.00–2.60 (m, 3H, cyclohexyl-CH, CH$_2$), 2.51–2.40 (m, 2H, CH$_2$), 2.07–1.98 (m, 2H, cyclohexyl-CH$_2$), 1.80–1.11 (m, 20H, 4×cyclohexyl-CH$_2$), 2×CH(CH$_3$)$_2$)

9. Identical Diesters

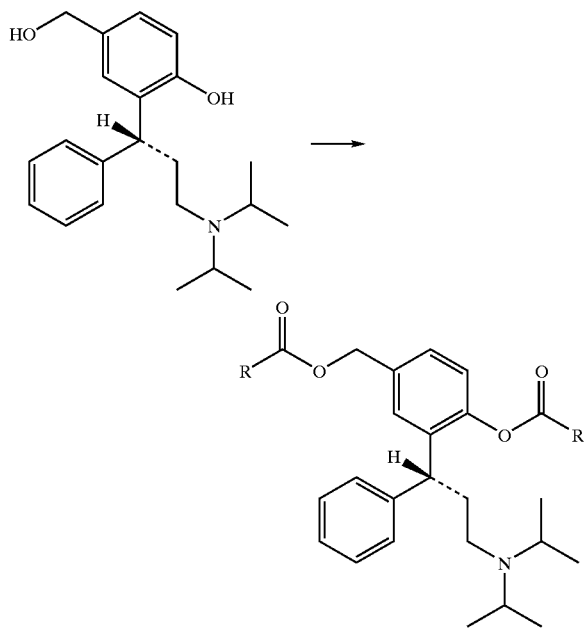

General Work Specification for the Manufacture of Identical Diesters

Into a solution of 7.30 g (21.4 mmol)R-(+)-2-(3-diisopropylamino-1-phenylpropyl)-4-hydroxyphenol (6) in 100 ml dichloromethane, under agitation at 0° C., a solution of acid chloride (49.2 mmol) in 50 ml dichloromethane is dropped. Then triethylamine-dichloromethane (6.86 ml/49.2 mmol-50 ml) is added. After 1–3 hours at room temperature the thin layer chromatography shows that conversion is complete. The deposit is washed successively with respectively 100 ml water, aqueous 0.1N-hydrochloric acid, 5 ml 5% aqueous sodium-hydrogen carbonate solution, 5 ml water, dried via, sodium sulphate and following filtration concentrated until dry. Then it is dried in the high-vacuum until constant weight.

The following compounds are, by way of example, manufactured using this method:

R=Methyl
R-(−)-acetic acid-2-(3-diisopropylamino-1-phenyl-propyl)-4-acetoxymethyl-phenyl-ester, free base Pale yellow oil, purity (HPLC): 95.2%.
$^{13}$C-NMR (CDCl$_3$): 20.36, 20.69, 20.94, 20.99, 36.41, 42.27, 43.69, 48.79, 65.89, 122.89, 126.28, 127.17, 127.92, 128.36, 133.69, 136.95, 143.61, 148.46, 168.97, 170.76.
LC-MS: 425 (15%, M$^+$), 410 (97%), 382 (4%), 308 (3%), 266 (7%), 223 (27%), 195 (13%), 165 (8%), 114 (100%).
$[\alpha]_D^{20}$=−33.1 (c=1, CH$_3$CN).
DC (1): 0.79.

R=Cyclohexyl
R-(+)-cyclohexane carboxylic acid-2-(3-diisopropylamino-1-phenyl-propyl)-4-cyclohexylcarbonyloxymethyl-phenyl-ester Pale yellow oil, purity (NMR): >95%.
$^{13}$C-NMR (CDCl$_3$): 20.30, 25.17, 25.58, 25.73, 28.97, 29.12, 41.70, 43.15, 44.03, 48.64, 65.37, 122.67, 125.88, 126.24, 127.06, 127.31, 127.90, 128.37, 134,03, 136.85, 143.55, 148.33, 174.20, 175.72.
DC (1): 0.96.

R=Isopropyl
R-(+)-isobutyrate-2-(3-diisopropylamino-1-phenyl-propyl)-4-isobutyryloxymethyl-phenyl-ester Free base: pale yellow oil, purity (HPLC): 95.6%.

$^{13}$C-NMR (CDCl$_3$): 18.96, 19.08, 20.59, 33.98, 34.20, 36.86, 41.72, 43.72, 48.72, 65.58, 122.65, 126.19, 126.73, 127.91, 128.11, 128.36, 133.91, 136.96, 143.81, 148.41, 175.15, 176.77.
DC (1): 0.74.
Hydrogen fumarate salt: colourless syrup, 94.4% HPLC purity.
$^{13}$C-NMR (CDCl$_3$): 17.89, 18.07, 18.94, 18.97, 19.07, 31.22, 33.93, 34.13, 41.78, 45.62, 53.93, 65.33, 122.93, 126.82, 127.45, 127.53, 127.91, 128.75, 134.74, 135.29, 135.42, 142.04, 148.44, 170.24, 175.71, 176.79.

R=4-(t-C$_4$H$_9$ CO$_2$)-C$_6$H$_4$
R-4-(t-butylcarbonyloxy)-benzoic acid-2-(3-diisopropylamino-1-phenyl-propyl)-4-(4-t-butylcarbonyloxymethyl-benzoic acid)-phenyl-ester hydrochloride Colourless crystals, melting point 105–7° C.
$^{13}$C-NMR (DMSO-d$_6$): 16.49, 16.71, 17.97, 18.06, 26.84, 31.36, 38.45, 41.70, 45.24, 53.79, 53.96, 55.09, 66.11, 122.47, 122.62, 123.59, 126.42, 126.83, 127.21, 127.70, 127.88, 128.02, 128.62, 131.17, 131.86, 134.48, 135.64, 142.52, 148.35, 154.86, 155.39, 163.80, 165.09, 176.14, 176.19.

10. Mixed Diesters

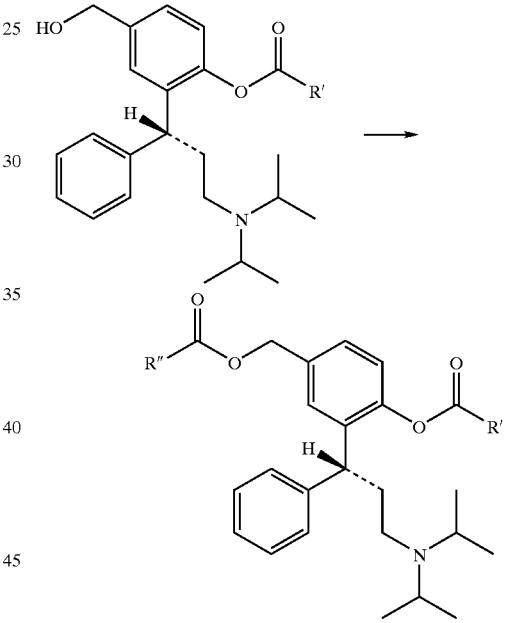

R′ is not equal to R″

General Work Specification for the Manufacture of Mixed Diesters

Into a solution of 5.30 mmol phenolic monoester of general formula A in 40 ml dichloromethane under agitation at 0° C. a solution of acid chloride (5.83 mmol) in 15 ml dichloromethane is dropped. Then triethylamine-dichloromethane (0.589 g/5.82 mmol-15 ml) is added. After 18 hours at room temperature the thin layer chromatography shows that conversion is complete. The deposit is washed successively with respectively 50 ml water, aqueous 0.1N-hydrochloric acid, 5 ml 5% aqueous sodium-hydrogen carbonate solution, 5 ml water, dried via sodium sulphate and following filtration concentrated until dry. Then it is dried in the high-vacuum until constant weight.

The following example is manufactured using this method:
R′=CH(CH$_3$)$_2$
R″=CH$_3$ R-(+)-isobutyrate-2-(3-diisopropylamino-1-phenyl-propyl)-4-acetoxymethyl-phenyl-ester Colourless oil.

DC (1): 0.56

$^{13}$C-NMR (CDCl$_3$): 19.12, 20.65, 21.05, 34.24, 37.02, 41.79, 43.79, 48.72, 65.98, 122.75, 125.98, 126.22, 127.94, 128.39, 128.84, 133.55, 137.04, 143.84, 148.58, 170.84, 175.18.

Hydrochloride: colourless crystals $^{13}$C-NMR (CDCl$_3$): 16.89, 17.04, 18.31, 18.92, 20.95, 31.49, 34.07, 41,64, 46.17, 54.55, 65.49, 122.91, 126.61, 126.93, 127.48, 127.83, 128.74, 134.50, 134.88, 141.61, 148.44, 170.67, 175.63.

$[\alpha]_D^{20}$=14.6 (c=1, CHCl$_3$).

What is claimed is:

1. Compounds of general formula I

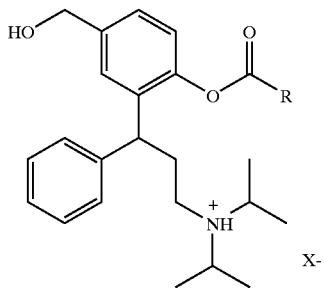

Formula I in which R denotes C$_1$–C$_6$-alkyl, C$_3$–C$_{10}$-cycloalkyl, substituted or unsubstituted phenyl and X$^-$ is the acid residue of a physiologically compatible inorganic or organic acid.

2. Compounds in accordance with claim 1, characterised in that X$^-$ in each case is an acid ester of hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+) -tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid.

3. Compounds in accordance with claims 1, characterised in that they have general formula 2:

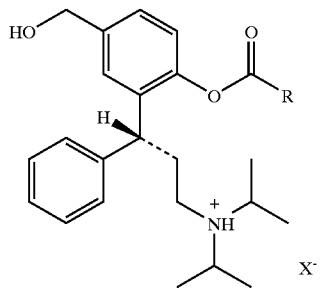

Formula 2 in which R denotes C$_1$–C$_6$-alkyl, C$_3$–C$_{10}$-cycloalkyl, substituted or unsubstituted phenyl and X$^-$ is the acid residue of a physiologically compatible inorganic or organic acid.

4. Compounds in accordance with claim 3, characterised in that X in each case is an acid ester of hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(−)-malic acid, D-(+)-malic acid, DL-tartaric acid, L-(+)-tartaric acid, D-(−)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid.

5. Compounds in accordance with claims 3, characterised in that they are R-(+)-2-(3-(diisopropylamino-1-phenylpropyl)-4-hydroxymethyl -phenylisobutyrate ester hydrogen fumarate, R-(+)-2-(3-(diisopropylamino-1-phenylpropyl)-4-hydroxymethylphenylisobutyrate ester-hydrochloride hydrate.

6. Compounds in accordance with claims 3, characterised in that R stands for cyclopropyl, cyclobutyl, cyclopentyl, cyclohexyl, 4-(1-cyclopropyl-methanoyloxy)-phenyl, 4-(1-cyclobutyl-methanoyloxy)-phenyl, 4-(1-cyclohexyl-methanoyloxy)-phenyl or 4-(2,2-dimethyl-propanoyloxy)-phenyl and X$^-$ denotes chloride.

7. Method for manufacturing compounds of general formula I

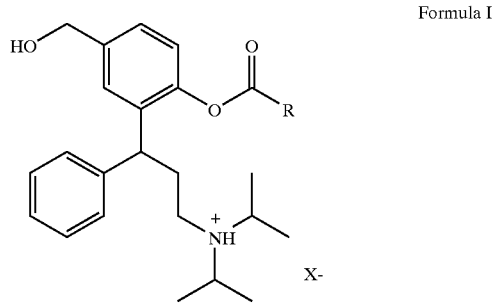

Formula I in which R denotes C$_1$–C$_6$-alkyl, C$_3$–C$_{10}$-cycloalkyl, substituted or unsubstituted phenyl and X– is the acid residue of a physiologically compatible inorganic or organic acid, characterised in that a) a compound of formula III

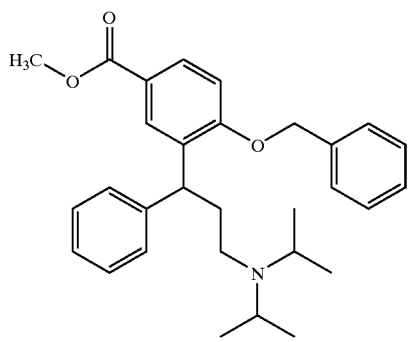

Formula III is split with a hydrogenation agent to form a compound of Formula V

Formula V

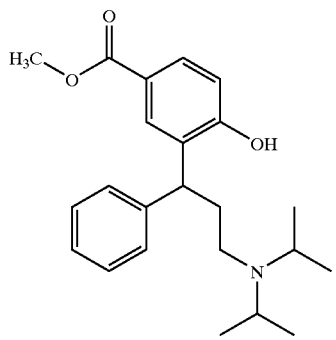

whereupon b) the compoud of formula V so obtained is converted with a reducing agent, in order to give a compound of formula VI Formula VI

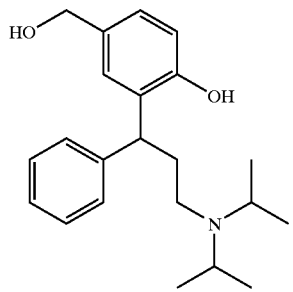

which c) is converted with an acylation agent, in order to obtain a compound of formula A Formula A

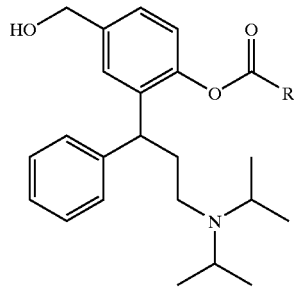

in which R has the significance stated above, which d) is converted with a physiologically compatible inorganic or organic acid to form a compound of formula I Formula I

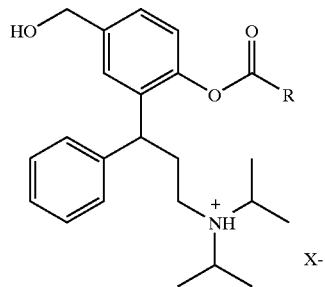

in which R denotes $C_1$–$C_6$-alkyl, $C_3$–$C_{10}$-cycloalkyl, unsubstituted or substituted phenyl and X– is the acid residue of a physiologically compatible inorganic or organic acid.

8. Method in accordance with claim 7, characterised in that for the manufacture of the compounds of general formula I hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(–)-malic acid, D-(+)-malic acid, DL-tartaric acid, L-(+)-tartaric acid, D-(–)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid are used.

9. Method for manufacturing compounds of general formula 2

Formula 2

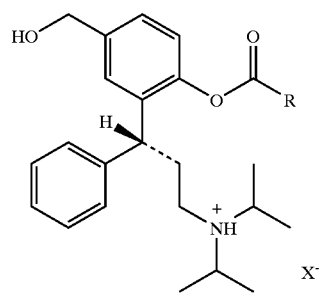

in which R denotes $C_1$–$C_6$-alkyl, $C_3$–$C_{10}$-cycloalkyl, substituted or unsubstituted phenyl and X– is the acid residue of a physiologically compatible inorganic or organic acid, characterised in that a) a compound of the formula 3

Formula 3

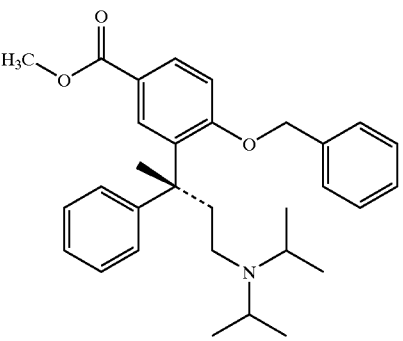

s split with a hydrogenation agent to form a compound of formula 5

Formula 5

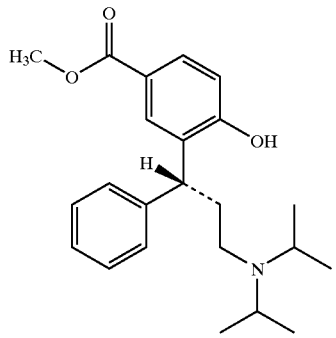

whereupon b) the compound formula 5 so obtained is converted with a reducing agent, in order to give a compound of formula 6

Formula 6

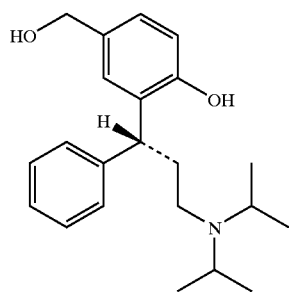

which c) is converted with an acylation agent, in order to obtain a compound of formula 1

Formula 1

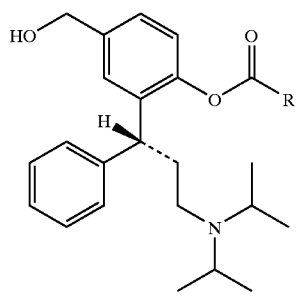

in which R has the significance stated above, which d) is converted with a physiologically compatible inorganic or organic acid to form a compound of formula 2

Formula 2

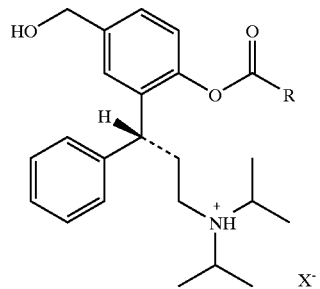

in which R denotes $C_1$–$C_6$-alkyl, $C_3$–$C_{10}$-cycloalkyl, unsubstituted or substituted phenyl and X– is the acid residue of a physiologically compatible inorganic or organic acid.

10. Method in accordance with claim 9, characterised in that for the manufacture of the compounds of general formula 2 hydrochloric acid, hydrobromic acid, phosphoric acid, sulphuric acid, nitric acid, acetic acid, propionic acid, palmitic acid, stearic acid, maleic acid, fumaric acid, oxalic acid, succinic acid, DL-malic acid, L-(–)-malic acid, D-(+)-malic acid, DL-tartaric acid, L-(+)-tartaric acid, D-(–)-tartaric acid, citric acid, L-aspartic acid, L-(+)-ascorbic acid, D-(+)-glucuronic acid, 2-oxopropionic acid (pyruvic acid), furan-2-carboxylic acid (mucic acid), benzoic acid, 4-hydroxybenzoic acid, salicyclic acid, vanillic acid, 4-hydroxycinammic acid, gallic acid, hippuric acid (N-benzoyl-glycine), aceturic acid (N-aectylglycine), phloretinic acid (3-(4-hydroxyphenyl)-propionic acid), phthalic acid, methanesulfonic acid or orotic acid are used.

11. Method in accordance with claims 7, characterised in that as the hydrogenation agent, Raney nickel/$H_2$ in methanol is preferably used as the solvent.

12. Method in accordance with claims 7, characterised in that for the reducing agent NaBH$_4$EtOH, preferably LiAlH$_4$/THF, is used.

13. Method in accordance with claims 7, characterised in that for the acylation agent isobutyrylchloride and for the base triethylamine are used.

14. Method in accordance with claims 9, characterised in that a compound of general formula 6 is converted with an equivalent isobutyryl chloride in the presence of triethylamine using one of the respective solvents ethylacetate, dichloromethane, tetrahydrofurane, acetonitrile or toluene regio- and chemoselectively into R-(+)-2-(3-diisopropylamino-1-phenylpropyl)-4-hydroxymethylphenylisobutyrate.

15. Method in accordance with claims 9, characterised in that R-(+)-2-(3-diisopropylamino-1-phenylpropyl)-4-hydroxymethylphenylisobutyrate ester and fumaric acid or hydrochloric acid are converted with the formation of the respective salt.

16. Method in accordance with claims 9 for the manufacture of R-(+)-2-(3-diisopropylamino-1-phenyl-propyl)-4-hydroxy-methylphenylisobutyrate ester hydrochloride hydrate, characterised in that the phenolic esterification of R-(+)-2-(3-diisopropylamino-1-phenylpropyl)-4-hydroxy-methylphenol (6) is carried out without the addition of an external base, in that solutions of (6) are dropped into solutions of isobutyryl chloride, that contain at least 1 mole equivalent of water, in order to directly obtain a corresponding stable, hydrate-containing hydrochloride.

17. Compound of formula 7

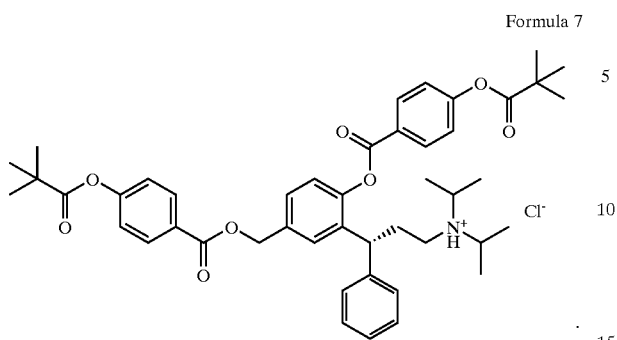

Formula 7

18. A method of manufacture of phenolic monoesters of general formula 1

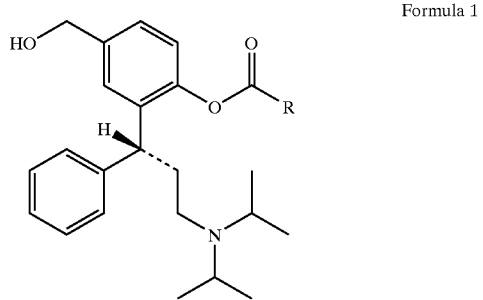

Formula 1 wherein the method comprises the steps of:

providing a compound of claim 17;

deprotecting the hydroxyl residues of the 4-hydroxybenzyl alcohol residue; and acylating the phenol residue.

19. A method of manufacture of salts of phenolic monoesters of general formula 2:

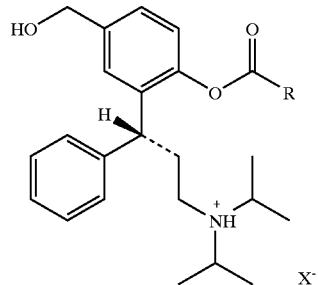

Formula 2 in which R denotes $C_1$–$C_6$-alkyl, $C_3$–$C_{10}$-cycloalkyl, substituted or unsubstituted phenyl and $X^-$ is the acid residue of a physiologically compatible inorganic or organic acid, wherein the method comprises the steps of:

providing a compound of claim 17;

deprotecting the hydroxyl residues of the 4-hydroxybenzyl alcohol residue; and acylating the phenol residue.

20. A method of manufacture of R-(+)-2-(3-diisopropylamino-1-phenylpropyl)-4-hydroxymethylphenylisobutyrate ester hydrogen fumarate or R-(+)-2-(3-diisopropylamino-1-phenylpropyl)-4-hydroxymethylphenylisobutyrate ester hydrochloride hydrate, the method comprising the steps of;

providing a compound of claim 17;

deprotecting the hydroxyl residues of the 4-hydroxybenzyl alcohol residue; and acylating the phenol residue.

21. A method of treating a patient suffering from urinary incontinence, which method comprises the step of administering to said patient an effective amount of a compound according to claim 1.

22. A method of treating a patient suffering from urinary incontinence, which method comprises the step of administering to said patient an effective amount of a compound according to claim 3.

23. A method of treating a patient suffering from urinary incontinence, which method comprises the step of administering to said patient an effective amount of a compound according to claim 5.

24. The method of any one of claims 21–23, wherein the urinary incontinence disorder is urge incontinence.

* * * * *

UNITED STATES PATENT AND TRADEMARK OFFICE
CERTIFICATE OF CORRECTION

PATENT NO. : 6,858,650 B1
DATED : February 22, 2005
INVENTOR(S) : Meese

It is certified that error appears in the above-identified patent and that said Letters Patent is hereby corrected as shown below:

Column 1,
Line 17, please correct "prodrugn" to -- prodrugs --
Line 26, please correct "3,3-diphenylpropylarines" to -- 3,3-diphenylpropylamines --

Column 3,
Line 50, please correct "and X" to -- and X⁻ --

Column 4,
Lines 45-46, please correct "are that" to -- are manufactured in that --

Column 5,
Line 24, please correct "with agent" to -- with a reducing agent --

Column 13,
Line 14, please correct "photometer. model" to -- photometer model --
Line 64, please correct "43.63" to -- 43.83 --

Column 15,
Line 37, please correct "amorphous. solid" to -- amorphous solid --

Column 16,
Line 37, please correct "125:59" to -- 125.59 --

Column 17,
Line 6, please correct "$[I]_D^{20=+6.0}$" to -- $[I]_D^{20}= +6.0$ --
Line 23, please correct "Ms" to -- MS --

Column 23,
Line 13, please correct "=14.6" to -- = +14.6 --
Line 47, "please correct "claims" to -- claim --

Column 24,
Lines 15 and 21, please correct "claims" to -- claim --
Line 46, please correct "physicologically" to -- physiologically --

UNITED STATES PATENT AND TRADEMARK OFFICE
CERTIFICATE OF CORRECTION

PATENT NO.    : 6,858,650 B1
DATED         : February 22, 2005
INVENTOR(S)   : Meese It is certified that error appears in the above-identified patent and that said Letters Patent is hereby corrected as shown below:

Column 28,
Lines 35, 38, 41, 45, 53 and 58, please correct "claims" to -- claim --

Column 30,
Line 17, please correct "physicologically" to -- physiologically --

Signed and Sealed this

Ninth Day of August, 2005

JON W. DUDAS
*Director of the United States Patent and Trademark Office*